(12) United States Patent
Saheb et al.

(10) Patent No.: US 8,758,774 B2
(45) Date of Patent: Jun. 24, 2014

(54) BIVALENT VACCINE FOR MARINE FISH AND METHOD FOR MAKING THE SAME

(75) Inventors: Azad Ismail Saheb, Salmiya (KW); Ahmed Al-Marzouk, Salmiya (KW)

(73) Assignee: Kuwait Institute for Scientific Research, Safat (KW)

( * ) Notice: Subject to any disclaimer, the term of this patent is extended or adjusted under 35 U.S.C. 154(b) by 0 days.

(21) Appl. No.: 13/553,924

(22) Filed: Jul. 20, 2012

(65) Prior Publication Data
US 2014/0023685 A1    Jan. 23, 2014

(51) Int. Cl.
A61K 39/106    (2006.01)
(52) U.S. Cl.
USPC .......................................... 424/261.1
(58) Field of Classification Search
CPC .................................................. A61K 39/106
USPC ........................................................ 424/261.1
See application file for complete search history.

(56) References Cited

U.S. PATENT DOCUMENTS

| | | | |
|---|---|---|---|
| 3,862,313 A | 1/1975 | Fryer et al. | |
| 4,009,259 A | 2/1977 | Ament et al. | |
| 6,083,520 A | 7/2000 | Toneby | |
| 6,872,386 B2 | 3/2005 | Yang et al. | |
| 2003/0022359 A1* | 1/2003 | Sayre et al. | 435/257.2 |
| 2004/0047881 A1* | 3/2004 | Kyle | 424/195.17 |
| 2004/0175407 A1* | 9/2004 | McDaniel | 424/423 |
| 2007/0082008 A1* | 4/2007 | Harel et al. | 424/195.16 |
| 2007/0292521 A1* | 12/2007 | Kuo et al. | 424/490 |
| 2008/0044481 A1* | 2/2008 | Harel | 424/490 |
| 2009/0317424 A1* | 12/2009 | Yang et al. | 424/204.1 |
| 2013/0122025 A1* | 5/2013 | Harris et al. | 424/184.1 |

FOREIGN PATENT DOCUMENTS

| | | | |
|---|---|---|---|
| CN | 101028513 | * 11/2010 | ........... A61K 39/106 |
| WO | WO03/103692 A1 | 12/2003 | |
| WO | 2008/084125 | * 7/2008 | |
| WO | WO2008/084125 A2 | 7/2008 | |

OTHER PUBLICATIONS

Alonso, MC et al, Journal of Experimental Marine Biology and Ecology, vol. 244, pp. 239-252, 2000, Role of ciliates, flagellates and bacteriophages on the mortality of marine bacteria and on dissolved DNA concentration in laboratory experimental systems.*
Berk, S.G. et al, Trans. America Micros. Society, vol. 95(3), pp. 514-520, 1976, A Study of Feeding responses to Bacterial prey by Estuarine ciliates.*

(Continued)

Primary Examiner — Albert Navarro
Assistant Examiner — Ginny Portner
(74) Attorney, Agent, or Firm — Lowe Hauptman & Ham LLP

(57) ABSTRACT

A bivalent vaccine against *Scuticociliatosis, Vibriosis* and marine ich in zobaidy, sobaity and hamoor includes a formalin killed whole cell *Vibrio* encapsulated *Uronema* spp. The vaccine is made by collecting a mass of infected zobaidy and scraping the moribund fish with a plastic spatula to transfer live *Uronema* into a pretri dish. The cerebro-spinal fluid is removed from the zobaidy and added to the fluid containing the *Uronema* at different concentrations formed with the BHIB. A mass of zobaidy juvenile are fed a commercial pellet feed coated with formalin inactivated *Uronema* spp. encapsulated in *Vibrio* four times a day for a period of ten days.

4 Claims, 5 Drawing Sheets

| Days post vaccination | Fry | | | Juveniles |
|---|---|---|---|---|
| | HD | MD | LD | |
| 51 dpv | 22.92 ± 14.73 | 11.81 ± 0.98 | 5.56 ± 7.86 | - |
| 80 dpv | 44.29 ± 22.22 | 34.29 ± 8.08 | 32.15 ± 25.25 | - |
| 110 dpv | 52.38 ± 43.64 | 47.62 ± 45.92 | 42.06 ± 36.45 | 84.62 ± 11.21 |

(56) References Cited

OTHER PUBLICATIONS

Al-Marzouk, Ahmed et al, Growth kinetics, protease activity and histophagous capability of Uronema sp. infesting culured silver pomfret Pampus argenteus in Kuwait, Dieases of Aquatic Organisms, vol. 76, Jun. 7, 2007, pp. 49-56.*
Al-Marzouk, A. et al., Culture of zobaidy Papmpus argenteus in Kuwait Phase-I, Kuwait Institute for Scientific Research, KISR Report No. 6910, 2003.
Azad, I.S. et al., Scuticociliatosis-associated mortalities and histopathology of natural infection in cultured . . . , Kuwait, Aquaculture 262:202-210, 2007.
Bai, S.C. et al., Present status and future prospects of aquaculture in Korea, World Aquacul. 32, 28-32, 2001.
Banik, N.L. et al., Inhibition of proteolysis by a cyclooxygenase inhibitor, Indomethacin Neurochem. Res. 25, 1509-1515, 2000.
Cawthorn, R.J., Overview of "Bumper car disease"—impact on the North American lobster fishery, Int. J. Parasitol, 27, 167-172, 1997.
Cheung, P.J. et al., Studies on the morphology of Uronema marinum Dujardin (Ciliatea: Uronematidae) with . . . , J. Fish Dis. 3, 295-303, 1980.
Clem, L.W. et al., Journal of Experimental Medicine, 125: 893-920, 1969.
Deveney, M.R. et al., A parasite survey of farmed Southern bluefin tuna, Thunnus maccoyii (Castelnau), J. Fish Dis. 28, 279-284, 2005.
Dykova, I. et al., Histopathological changes in turbot Scophthalmus maximus due to a histophagous ciliate, Dis. Aquat. Org. 18, 5-9, 1994.
Ellis, A.E., Fish Vaccination (Ed. A.E. Ellis), Academic Press, London, p. 1-19, 1988.
Ferguson, H.W. et al., Cranial ulceration in Atlantic salmon Salmo salar associated with Tetrahymena sp., Dis. aquat. Org. 2, 191-195, 1987.
Gill, P.A. et al., Ulcerative dermatitis associated with Uronema sp. infection of farmed sand whiting Sillago ciliata, Aust. Vet. J. 75, 357, 1997.
Hildemann, W.H., American Naturalist, 96:195-204, 1962.
Hoffmann, G.L. et al., A disease of freshwater fishes caused by Tetrahymena corlissi Thompson, 1955, and a key for identification . . . , J. Parasitol. 61, 217-223, 1975.
Iglesias, R. et al., Philasterides dicentrarchi (Ciliophora, Scuticociliatida) as the causative agent of scuticociliatosis in farmed . . . , Dis. Aquat. Org. 46, 47-55, 2001.
Iglesias, R. et al., Antiprotozoals effective in vitro against the scuticociliate fish pathogen Philasterides dicentrarchi, Dis. Aquat. Org. 49, 191-197, 2002.
Imai, S. et al., Tetrahymena infection in guppy, Poecilia reticulata, Fish Pathol. 35, 67-72, 2000.
Jee, B.Y. et al., Morphology and biology of parasite responsible for scuticociliatosis of cultured olive flounder Paralichthys olivaceus, Dis. Aquat. Org. 47, 49-55, 2001.
Joosten, P.H.M. et al., Oral vaccination of fish against Vibrio anguillarumusingalginate microparticles, J. Fish & Shellfish Immunol., vol. 7, No. 7, pp. 471 1997.
Jung, S.H. et al., Formaldehyde residues in formalin-treated olive flounder (Paralichthys olivaceus), black rockfish (Sebastes schlegeli) . . . , Aquaculture 194, 253-262, 2001.
Jung, S.J. et al., Complete small subunit rRNA gene sequence of the scuticociliate Miamiensis avidus pathogenic to olive flounder . . . , Dis. Aquat. Organ. 64, 159-162, 2005.
Kim, S.M. et al., Pseudocohnilembus persalinus (Ciliophora: Scuticociitida) is an additional causing species of scuticociliatosis . . . , Dis. Aquat. Org. 62, 239-244, 2004b.
Kim, S.M. et al., Occurrence of scuticociliatosis in olive flounder Paralichthys olivaceus by Philasterides dicentrarchi. . . , Dis. Aquat. Org. 62, 233-238, 2004a.
Korea National Statistical Office, 2001, pages?.
Kovacs, P. et al., Indomethacin alters phospholipid and arachidonate metabolism in Tetrahymena pyrifiormis, Comp. Biochem. Physiol. C. 117, 311-315, 1997.

Kovacs, P. et al., Effects of indomethacin on the divisional morphogenesis and cytoskeleton-dependent processes of Tetrahymena, Cell Biochem Funct. 21, 169-175, 2003.
Kwon, S.R. et al., Differences between short and long term cultures of Uronema marinum (Ciliophora: Scuticociliatida) in chemiluminescence . . . , Aquaculture 221, 107-114, 2003.
Lee, E.H. et al., Measurement of protease activity of live Uronema marinum (Ciliata: Scuticociliatida) by fluorescence polarisation, Dis. Aquat. Org. 54, 85-88, 2003.
Leiro, J. et al., Effects of the histophagous ciliate Philasterides dicentrarchi on turbot phagocyte responses, Fish Shellfish Immunol. 17, 27-39, 2004.
Marchalonis, J.J., Immunology, 20:161-173, 1971.
Martin Perez-Santos, J.L., In vitro indomethacin administration upregulates interleukin-12 production and polarizes the immune . . . , Parasite Immunol. 23, 599-606, 2001.
McKerrow, J.H., Parasite proteases, Experimental Parasitology, 68, 111-115, 1989.
McKerrow, J.H. et al., The proteases and pathogenicity of parasitic protozoa, Annu. Rev. Micribiol. 47, 821-853, 1993, abstract only.
Morado, J.F. et al., Ciliate parasites and related diseases of crustacea: A review, Rev. Fish Sci. 3, 275-354, 1995, abstract only.
Munday, B.L. et al., Fatal encephalitis due to the scuticociliate Uronema nigricans in sea-caged, southern bluefin tuna Thunnus maccoyii, Dis. Aquat. Org., 30, 17-25, 1997.
North, M.J., The Characteristics of Cysteine Proteinases of Parasitic Protozoa, Biol. Chem. 373, 401-406, 1992, abstract only.
Oh, M.J. et al., Susceptibility of marine fish species to a megalocytivirus, turbot iridovirus, isolated from turbot Psetta maximus (L.), J. Fish Dis. 29, 415-421, 2006.
Papermaster, B.W. et al., Evolution of the Immune Response, Journal of Experimental Medicine, 119:105-130, 1964.
Parama, A. et al., Cysteine proteinase activities in the fish pathogen Philasterides dicentrarchi (Ciliophora: Scuticociliatida), Parasitology 128, 541-549, 2004.
Parker, J.G., Cultural characteristics of the marine ciliated protozoan, Uronema marinum Dujardin, J. Exp. Marine Biol. & Ecol., vol. 24, No. 3, pp. 213-226, 1976, abstract only.
Quintela, J.M. et al., Piperazine N-substituted naphthyridines, pyridothienopyrimidines and pyridothienotriazines: new . . . , Eur. J. Med. Chem. 38, 265-275, 2003.
Rombout, J.H.W.M. et al., Developmental and Comparative Immunology, 17:55-66, 1993.
Rosenthal, P.J., Proteases of protozoan parasites, Adv. Parasitol. 43, 105-159, 1999.
Singh, D. et al., Role of cysteine proteinase of Entamoeba histolytica in target cell death, Parasitol., 129, 127-135, 2004.
Speare, D.J., Disorders associated with exposure to excess . . . , Fish Diseases and Disorders, Non-Infectious Disorders, vol. 2, CABI Publishing, Oxon, pp. 207-224, 1998.
Statistical Year Book of Maritime Affairs and Fisheries, The production of flounder cultured in shallow . . . , Ministry of Maritime Affairs and Fisheries, Korea, p. 1068, 2000, six pages?
Sterud, E. et al., Systemic infection with Uronema-like ciliates in farmed turbot, Scophthalmus maximus (L.), J. Fish Dis. 23, 33-37, 2000.
Thompson Jr., C.L., Miamiensis avidus, a marine facultative parasite in the ciliate order Hymenostomatida, J. Protozool. 11, 378-381, 1964.
Tsutsumi, V. et al., Experimental amebiasis: a selected review of some in vivo models, Arch Med. Res. 37, 210-220, 2006.
Uchida, D. et al., Comparative Biochemistry and Physiology, Part B, 127:525-532, 2000.
Yoshinaga, T. et al., Isolation and in vitro cultivation of an unidentified ciliate causing scuticociliatosis in Japanese flounder . . . , Gyobyo Kenkyu, 28, 131-134, 1993.
Zuo, X et al., In vitro haemolysis of piscine erythrocytes by purified metallo-protease from the pathogenic haemoflagellate . . . , Katz. J. Fish Dis. 23, 227-230, 2000.
Ahne, W., International Symposium of Fish Biologics: Serodiagnostics and Vaccines, Development of Biological Standards, 49:3-27, Leetown, WV, 1981.

(56) References Cited

OTHER PUBLICATIONS

Boettner, D.R. et al., *Entamoeba histolytica* activates host cell caspases during contact-dependent cell killing, Curr. Top. Microbiol. Immunol. 289, 175-184, 2004.

Daugschies, A. et al., Eicosanoids in parasites and parasitic infections, Adv. in Parasitol, 46, 181-240, 2000.

Dorson, M., Role and Characterization of Fish Antibody, International Symposium of Fish Biologics: Serodiagnostics and Vaccines, Development of Biological Standardisation, 49:307-317, 1981.

Gould, R.W. et al., Spray Vaccination: A Method for the Immunization of Fish, Fish Pathology, 13:63-68, 1978.

McCarthy, D.H., Detection of *Aeromonas salmonicida* Antigen in Diseased Fish Tissue, Journal of General Microbiology, 88:384-386, 1975.

Oh, D.H. et al., A new rhabdovirus (HIRRV-Like) isolated in Korea from cultured olive flounder, J. Fish Pathol. 11, 129-136, 1998.

Oh, D.H. et al., Bacterial diseases in olive flounder farms on Cheju Island, Korea, J. Fish Pathol. 11, 23-27, 1998.

Parama, A. et al., Scuticociliate proteinases may modulate turbot immune response by inducing apoptosis in pronephric leucocytes, Int. J. Parasitol, 37, 87-95, 2007.

Roberson, B.S., Detection of Fish Antibody by Thin-Layer Elisa, International Symposium of Fish Biologics: Serodiagnostics and Vaccines, Leetown, WV, Development of Biological Standards, 49:113-118, 2000.

Shelton, E. et al., The Ultrastructure of Carp (*Cyprinus carpio*) Immunoglobulin: A Tetrameric Macroglobulin, Journal of Molecular Biology, 54:615-617, 1970.

Sommer, U. et al., Identification of *Trichomonas vaginalis* cysteine proteases that induce apoptosis in human vaginal epithelial cells, J. Biol. Chem., 280, 25, 23853-23860, 2005.

Terrazas, L.I. et al., *Taenia crassiceps* cysticercosis: a role for prostaglandin E2 in susceptibility, Parasitol. Res. 85, 1025-1031, 1999.

Tsafriri, A., Ovulation as a tissue remodeling process, Proteolysis and cumulus expansion, Adv. Exp. Med. Biol. 377, 121-140, 1995.

Bassleer, G., *Uronema marinum*, A New and Common Parasite on Tropical Salt-Water Fishes, Freshwater and Marine Aquarium 6, 14, 78-81, 1983.

Dragesco, A. et al., Philasterides dicentrarchi, n. sp., (Ciliophora, Scuticociliatida), a Histophagous Opportunistic Parasite of *Dicentrarchus labrax* (Linnaeus, 1758), a Reared Marine Fish, European Journal of Protistology, 31, 327-340, 1995.

Oh, M.J. et al., Detection of Birnavirus from Cultured Marine Fish Using Polymerase Chain Reaction (PCR), J. Fish Pathol. 12, 49-55, 1999.

Rath, R.K., Fish Diseases and Fish Health Management, Freshwater Aquaculture, 2nd Edition, Scientific Publishers, Jodhpur, India, pp. 253-263, 2000.

Sadowski, T. et al., Effects of non-steroidal antiinflammatory drugs and dexamethasone on the activity and expression of matrix metalloproteinase-1, matrix metalloproteinase-3 and tissue inhibitor of metalloproteinases-1 by bovine articular chondrocytes, Osteoarthritis and Cartilage 9, 407-415, 2001.

Van Der Heijden, M.H.T. et al., Production, characterisation and applicability of monoclonal antibodies to European eel (*Anguilla anguilla* L., 1758) immunoglobulin, Veterinary Immunology and Immunopathology, 45, 151-164, 1995.

\* cited by examiner

| Days post vaccination | Fry | | | Juveniles |
|---|---|---|---|---|
| | HD | MD | LD | |
| 51 dpv | 22.92 ± 14.73 | 11.81 ± 0.98 | 5.56 ± 7.86 | - |
| 80 dpv | 44.29 ± 22.22 | 34.29 ± 8.08 | 32.15 ± 25.25 | - |
| 110 dpv | 52.38 ± 43.64 | 47.62 ± 45.92 | 42.06 ± 36.45 | 84.62 ± 11.21 |

BIVALENT VACCINE FOR MARINE FISH AND METHOD FOR MAKING THE SAME

FIELD OF THE INVENTION

This invention relates to a bivalent vaccine for marine fish and a method for making the same. To be more specific, the invention relates to a bivalent vaccine against *Scuticociliatosis* and *Vibriosis* namely for silver pomfret or Zobaidy (*Pampus argenteus Euphrasen*), bluefin bream or Sobaity (*Sparidenax hasta*) and orange spotted grouper or Hamoor (*Epinephilus coioides*) the bivalent vaccine comprises and/or consists of formalin-killed *Vibrio*-encapsulated *Uronema* spp. and a method for making the same. The method includes the steps of production, inactivation and incorporating vaccine into food for zobaidy, sobaity and hamoor.

*Uronema* spp. provides an antigen similar to marine "ich" and hence this antigen provides cross protection against marine "ich." The second antigen is a *Vibrio, Vibrio alginolyticus* which is fed to *Uronema* spp. and the *vibrio*-encapsulated *Uronema* becomes a bivalent vaccine.

BACKGROUND FOR THE INVENTION

*Scuticociliatosis* caused by *Uronema* spp. is one of the most serious parasitic diseases of marine fish. The parasite has been reported to cause severe mortalities in cultured zobaidy, goat fish, sea horses etc. Antigenically similar and taxonomically related holotrichous ciliate, popularly known as marine "ich" *Cryptocaryon irritans*, is a serious parasite in all stages of sobaity, hamoor and zobaidy, causing almost a complete loss of cultured stock. *Vibrio* spp. have been associated with the opportunistic pathology of the weakened fish as it was seen in the case of zobaidy at the Kuwait Institute for Scientific Research (KISR) during 2005. (Note: An article by Azad et al., 2007).

Vaccines can provide a long term and effective remedy to these parasitic and bacterial infections in fish. However, the present invention takes care of difficulties and provides methods for the In vitro propagation and vaccine production of *Vibrio*-encapsulated *Uronema* spp. due to its antigenic similarity and taxonomic relatedness to protect against *scuticociliatosis* and marine ich. Also, the ability of the ciliate to feed on and concentrate *Vibrio* spp. in them will serve as a *Vibrio* and ciliate vaccine.

Fish aquaculture has been in vogue since times immemorial. Fish in aquaculture are susceptible to the threats of diseases. Fortunately, fish exhibit a very well developed immune system with the production of antibodies. Teleostean fishes are capable of eliciting a wide range of non-specific and specific immune responses that are comparable to the higher vertebrate immune systems (Clem, L. W. and Leslie, G. A., 1969. Journal of Experimental Medicine, 125:893-920; Hildemann, W. H. 1962. American Naturalist, 96:195-204; Ellis, A. E. 1988. Fish Vaccination (Ed. A. B. Ellis), Academic Press, London, P. 1-19).

Production of vaccine against parasites that are obligatory and cannot be cultured outside a fish host has been the major stumbling block in the production of commercial vaccines for marine fish. Holotrichous ciliates such as the 'ichs', *Ichthyopthirius multifiliis* (in freshwater fish), *Cryptocaryon irritans* (in marine fish) are the single most serious pathogens followed by opportunistic, yet increasingly threatening 'velvet' disease (*Tetrahymena* spp. in freshwater, *Philasterides* spp. and *Uronema* spp. in marine aquaculture systems).

Experimental immunization of catfish with *Ichthyophthirius multifiliis* has been reported (Becker et al., "Some Host Response of White Catfish to *Ichthyophthirius multifiliis* Fouquet", Proc. 18th Ann. Conf. S.E. Assoc. Game and Fish Comm., 1964). More studies have shown that channel catfish injected intraperitoneally with vaccine prepared from the ground trophozoites, with and without Freund's adjuvant, survived challenge whereas control suffered 100% mortality after seven days (Areerat, S., "The Immune Response of Channel Catfish, *Ictalurus punctatus* (Rafinesque) to *Ichthyophthirius multifiliis*", Masters Thesis, Auburn University, Auburn, Ala. (1974)). Clark et al. (1995) showed that the 'I' antigen of the freshwater 'ich' produces strongly immunogenic response in naïve channel catfish.

The scuticociliates, notably *Uronema* spp. *Miamiensis* spp. and *Philasterides* spp. have been increasingly becoming serious threats to cultured marine fish. *Uronema* spp. caused high mortalities in cultured silver pomfret (*Pampus argenteus*) in Kuwait during 2005 (Azad et al., 2007). Other scuticociliates have also been reported to cause severe losses in cultured fish in different countries (Thompson and Moewus, 1964; Cheung et al., 1980; Yoshinaga and Nakazoe, 1993; Dykova and Figueras, 1994; Dragesco et al., 1995; Gill and Calinan, 1997; Munday et al., 1997; Iglesias et al., 2001). *Uronema* spp. has also been reported from farmed sea bass (*Dicentrarchus labrax*) in the Mediterranean (Dragesco et al., 1995), Japanese flounder, *P. olivaceus* (Yoshinaga and Nakazoe, 1993). The bluefin tuna (*Thunnus maccoyii*) infected with *Uronema nigricans* (Munday et al., 1997) and *Uronema marinum* (Jee et al., 2001) has been previously reported.

A prior art article by Azad, I. S., A. Al-Marzouk, C. M. James, S. Almatar, H. Al-Gharabally. 2007 is entitled "*Scuticociliatosis*-associated mortalities and histopathology of natural infection in cultured silver pomfret (*Pampus argenteus Euphrasen*) in Kuwait. Aquaculture 262:202-210.

A further article by Bassleer, G., 1983 reports on "*Uronema marinum*, a new and common parasite on tropical saltwater fishes. Freshwater Mar. Aquar. 6, 78-81.

In addition, an article by Cheung, P. J., Nigrelli, R. F., Ruggieri, G. D., 1980 reports on studies on the morphology of *Uronema marinum* Dujardin (Ciliatea: Uronematidae) with a description of the histopathology of the infection in marine fishes. J. Fish Dis. 3, 295-303.

In addition, an article by Jee, B. Y., Kim, Y. C., Park, M. S., 2001 reports on morphology and biology of parasites responsible for *scuticociliatosis* of cultured olive flounder *Paralichthys olivaceus*. Dis. Aquat. Org. 47, 49-55.

Finally, an article by Sterud, E., Hansen, M. K., Mo, T. A., 2000 reports on the systemic infection with *Uronema*-like ciliates in farmed turbot, *Scophthalmus maximus* (L.). J. Fish Dis. 23, 33-37.

In addition to the above, there are several patents of interests. To be more specific:

PCT/ES2007/070217 entitled "Philasteroides scuticociliate Vaccine For Marine Fish." This patent discloses a method for preparing a vaccine against the principal pathogenous ciliates causing *scuticociliatosis* (genera. *Philasterides/Miamiensis* and *Uronema*) in farmed marine fish. The vaccine consists of trophozoites of the ciliates inactivated with formaldehyde and emulsified in an oil-based adjuvant. The vaccine administered to fish experimentally infected with the ciliates at concentrations from $10^4$ to $10^8$ cells per milliliter, inactivated with a concentration of formaldehyde less than 1% and emulsified in adjuvant at concentrations between 10 and 90%, led to a high degree of protection.

An earlier patent PCT/US2003/15408 relates to probiont and prebiont loaded zooplankton for improving health, growth and survival rates of larval fish, fish fry and crustaceans by feeding them probiont or prebiont-loaded zooplankton.

As reported therein production vaccine against parasites that are obligatory and cannot be cultured outside a fish host has been the major stumbling block in the production of commercial vaccines for marine fish. Holotrichous ciliates such as the "ich", Ichthyopthirius multifilius (in fresh water fish), cryptocaryon irritans (in marine fish) are the single most serious pathogens followed by opportunistic, yet increasingly "velvet" disease (Tetrahymena spp. in fresh water, philasterides spp. and Uronema spp. in marine aquaculture systems).

The object of the present invention is to provide a treatment useful as a prophylactic for the management of fish diseases in mariculture and its applications in other aquatic animals. A particular object of the present invention is to provide a method as useful for producing and delivering a bath-cum-oral whole-cell inactivated Uronema spp. vaccine the development of an immune prophylactic for use in fish health management.

More particularly, an object of the present invention is to provide a method for the oral/bath delivery of Vibrios exemplified through Vibrio alginolyticus bioencapsulated in Uronema sp. during the production of the vaccine for fish health management.

BRIEF SUMMARY OF THE INVENTION

The invention contemplates a bivalent vaccine against Scuticociliatosis, Vibriosis; and, against marine "ich" (Cryptocaryon irritans) which has antigenic similarity with Uronema spp. The bivalent vaccine comprising or consisting of forma-link-killed whole cell of Vibrio-enacapsulated Uronema spp. is for zobaidy, sobaity and hamoor.

The invention also contemplates a method for the production, inactivation and incorporation into feed of a bivalent Vibrio-encapsulated Uronema spp. for application in marine fish for protection against Scuticociliatosis and marine ich, the method comprising or consisting of the steps of:

collecting infected zobaidy, scraping the skin of moribound zobaidy and transferring live Uronema spp. into petri plates containing sterilized seawater, for further production:

removing the cerebro-spinal fluid of the infected zobaidy and isolating the ciliate parasite by passing the cerebro spinal fluid through 1 micron mesh filter and transferring the parasite to sterile seawater, adjusting the live parasite count to 100,000 cells per mL. The ciliate cell suspension was added for growing the ciliates at the rate of 1 mL per L of sterile brain heart infusion broth (BHIB) with 1.5% NaCl. The ciliate parasite is allowed to grow in the BHIB medium for 2-4 days. The virulence testing of the ciliate parasite is done by injecting 100,000 live cells into the peritoneal cavity of healthy live zobaidy. The process of infection was monitored and the infected fish were sacrificed for obtaining the ciliate from blood and cerebro-spinal fluid as explained above; and different concentrations of dilute BHIB (5-10% dilution with sterile phosphate buffered saline or PBS) is used to inoculate the parasitic ciliate for growth. Vibrio alginolyticus is grown in full strength BHIB for 24 h at room temperature. The bacterium is harvested and added to the ciliate culture medium at 1 mL of 1000 million cells for feeding the parasite. The co-culture of the ciliate and the bacterium is allowed for a further 2-4 days for incubation. The Vibrio encapsulated Uronema spp. is inactivated in the medium by adjusting the final formalin concentration to 0.5%. The inactivated Vibrio-encapsulated parasite is harvested when the cell count reaches the peak levels (generally 3-4 days) by spinning at 8000 rpm, washing the cells by resuspending them in sterile PBS and centrifuging again. This process is repeated 2-3 times to remove all the traces of formalin. The final harvested pellet of Vibrio-encapsulated Uronema spp. is resuspended in sterile PBS. The ciliate count was taken by counting 20-30 random drops of 100 microliter each of thoroughly mixed suspension. Similarly, bacteria was enumerated using plate count method on thiosulphate citrate bile salt sucrose (TCBC) agar as the growth medium.

The invention will now be described in connection with the accompanying figures.

TABLE 1

Figures 1A, 1B:
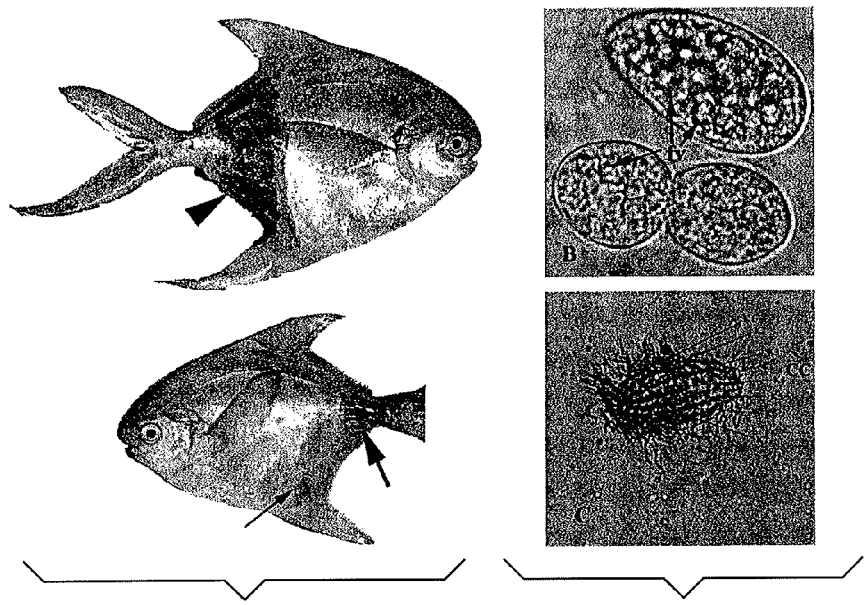
FIG. 1 represents Uronema spp. pathogenic in zobaidy (Pampus argenteus) at the infestation stage, isolated from the cerebro-spinal fluid and stained to reveal ciliary structure.
Figure 2:
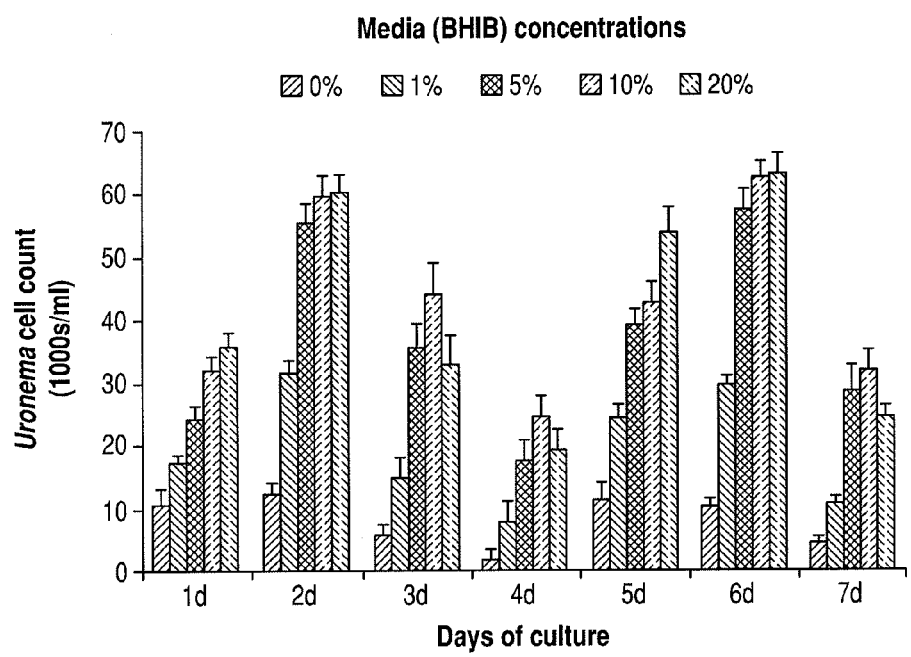
FIG. 2 represents the kinetics of the parasite, Uronema spp. production in defined artificial media, BHIB.
Figure 3:
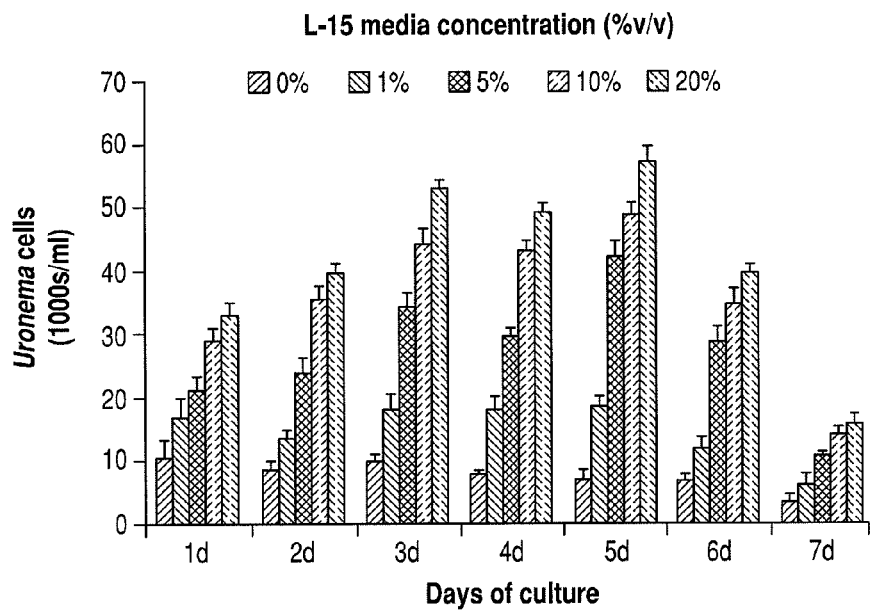
FIG. 3 represents the kinetics of the parasite, Uronema spp. production in defined artificial media, L-15.
Figure 4:
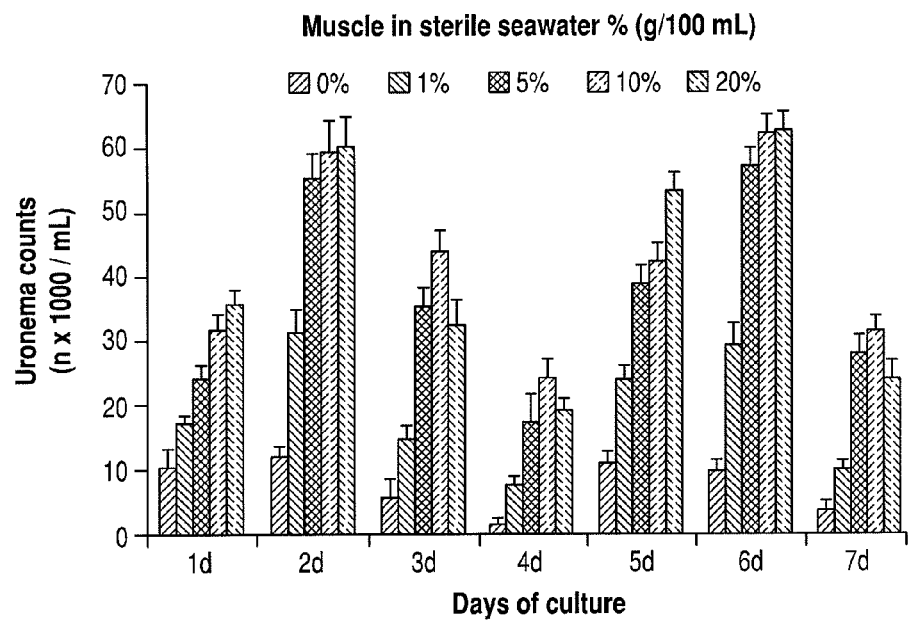
FIG. 4 represents the kinetics of the parasite, Uronema spp. production in artificial media containing silver pomfret muscle.
Figure 5A:
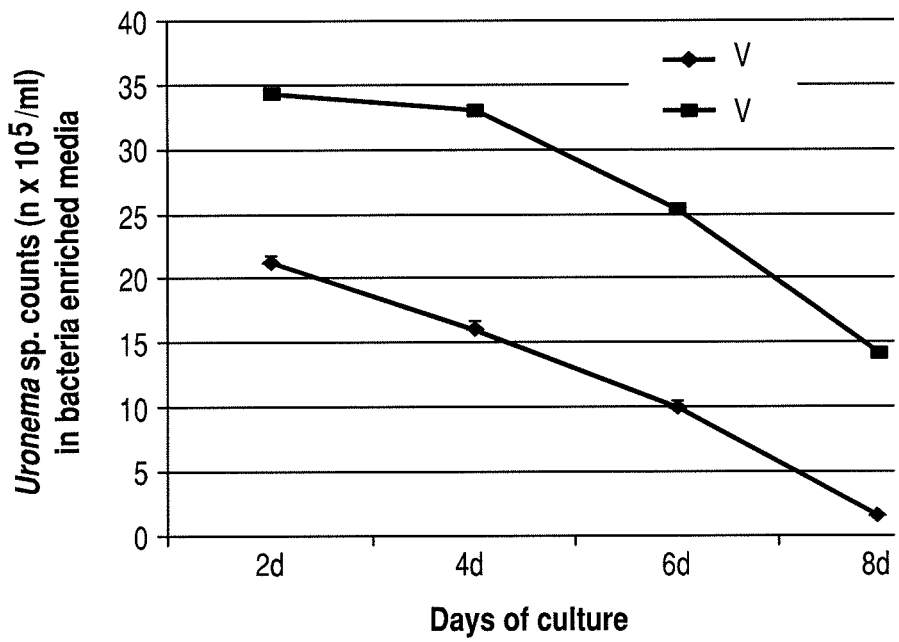
FIG. 5 a and b represent the kinetics of the parasite, Uronema spp. production in defined artificial media containing BHIB and Vibrio alginolyticus and V. harveyi inoculum.
Figure 5B:
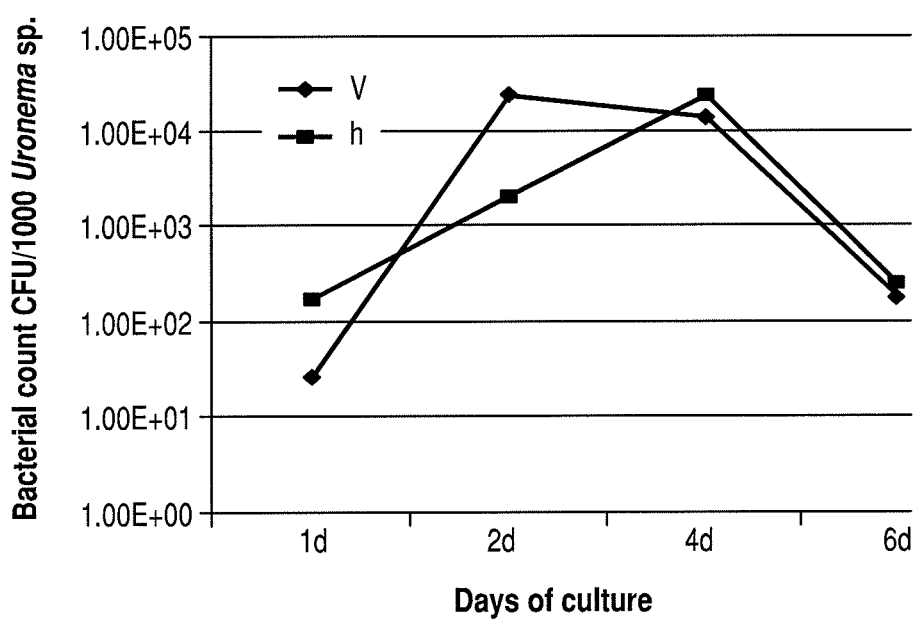
Figure 6:
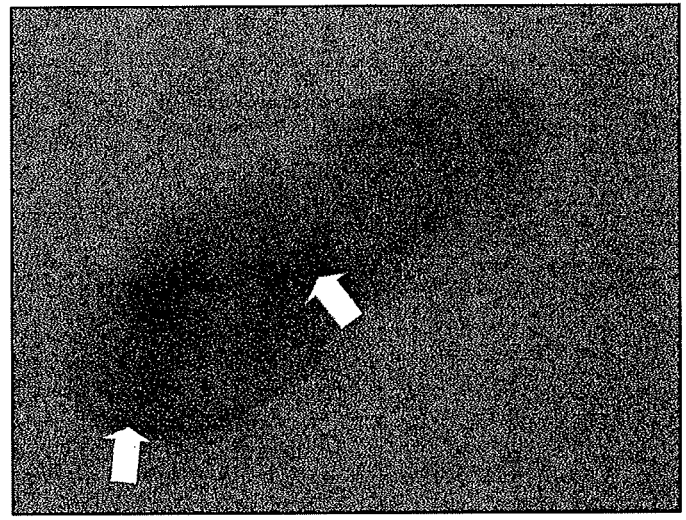
FIG. 6 represents the immunostaining showing immunogenicity of the cilia and mouth parts of Uronema spp.
Figure 7A:
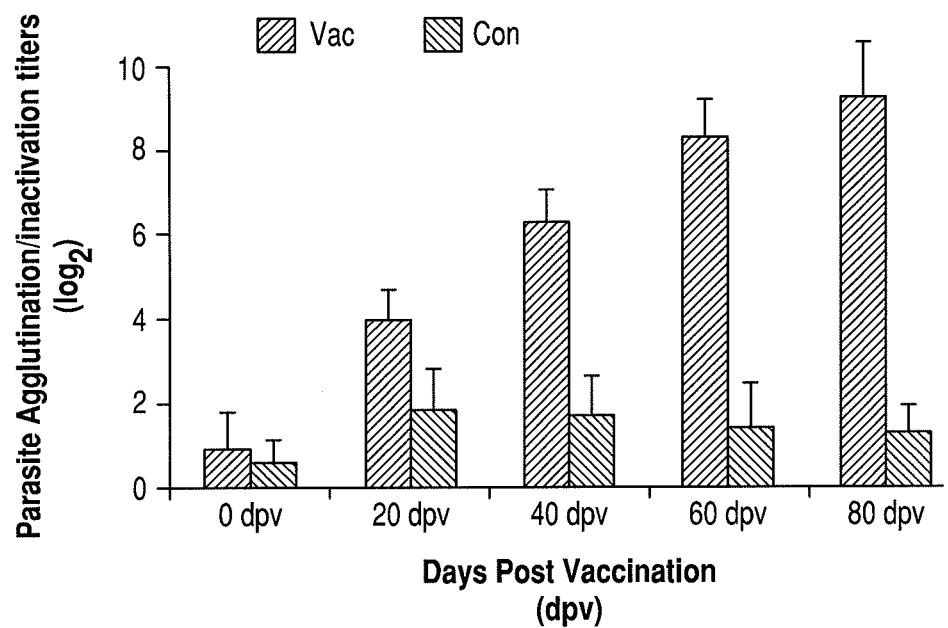
FIG. 7a represents the parasite inactivation/immobilization titers in orally vaccinated sobaity (Sparidentax hastia).
Figures 7B, 8:
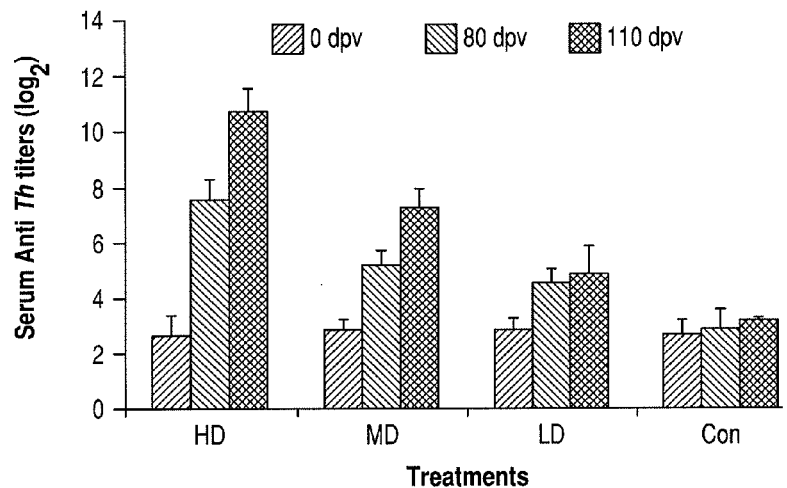
FIG. 7b represents the kinetics of fish antibody production expressed as serum agglutination titers in response to formalin inactivated V. harveyi in bi-valent vaccine-fed sobaity (Sparidentax hasta) fry.
FIG. 8 shows the inactivation of Uronema using the mucous of orally vaccinated Zobaidy with a priming dose for ten days and the relative inactivation due to a booster vaccination (BS) of a ten day vaccine feeding after one month of the primary vaccination.

Protective Response Data of Vibrio-encapsulated Uronema spp. Vaccine-Fed and Control Fry of Sobaity Challenged with a Combination of Uronema spp. and V. harveyi.

| Days post vacci- | Fry | | | |
| --- | --- | --- | --- | --- |
| nation | HD | MD | LD | Juveniles |
| 51 dpv | 22.92 ± 14.73 | 11.81 ± 0.98 | 5.56 ± 7.86 | — |
| 80 dpv | 44.29 ± 22.22 | 34.29 ± 8.08 | 32.15 ± 25.25 | — |
| 110 dpv | 52.38 ± 43.64 | 47.62 ± 45.92 | 42.06 ± 36.45 | 84.62 ± 11.21 |

The accompanying Table 1 represents protective response of Vibrio-encapsulated Uronema spp.—fed sobaity (Sparidentax hasta) to a combination challenge with live Uronema injection and live V. harveyii injection.

DESCRIPTION OF THE PREFERRED EMBODIMENTS OF THE INVENTION

Accordingly, the present invention provides a method for the production, maintenance and harvesting of Uronema sp. in different culture media.

The method relates to the formalin-inactivation of *Uronema* sp. for incorporation into commercial feed for sobaity (*Sparidentax hasta*).

The present invention also relates to the method of bath vaccination of sobaity in formalin-inactivated *Uronema* sp. suspension.

An embodiment of the present invention relates to the method of incorporation of formalin-inactivated *Uronema* spp.

In a preferred embodiment of the present invention, the process of *Vibrio* encapsulation in *Uronema* spp. is described.

In still another embodiment of the present invention, sobaity juvenile (*Sparidentax hasta*) is used for oral vaccination.

In another embodiment of the present invention, the fish serum and mucus collection is explained for obtaining agglutination/immobilization titers against formalin-inactivated *Uronema* sp. and formalin-inactivated *Vibrio alginolyticus* and *V. harveyi* is explained.

In yet another embodiment of the present invention, the sobaity fish (*Sparidentax hasta*) is immunized with different doses of formalin-inactivated *Uronema* sp. and or formalin inactivated, *Vibrio*-enriched *Uronema* sp.

In one more embodiment of the present invention, serum or mucus collected from orally vaccinates sobaity (*Sparidentax hasta*) is titrated against formalin-inactivated *Uronema* sp. or formalin-inactivated *V. alginolyticus* and *V. harveyi*.

In another embodiment of the present invention, the serum from orally vaccinated sobaity (*Sparidentax hasta*) is immunostained by dot assay using fluorescene conjugated second antibody.

In another embodiment of the present invention, the orally vaccinated sobaity (*Sparidentax hasta*) is challenged with live and/or live *Vibrio harveyi*.

EXAMPLES

Example 1

Infected Zobaidy (*Pampus argenteus Euphrasen*), ranging from 65-200 g in weight were collected from the mariculture facilities of MFD, KISR. Skin of moribund fish were scraped using plastic spatula and the live *Uronema* sp. were transferred into petri plates containing sterile seawater for further purification. The cerebro-spinal fluid was removed using a sterile 22 gauge syringe and the fluid was used for isolating the ciliate. This formed the source material for the ciliate production and virulence testing.

Example 2

The ciliate was inoculated into different concentrations of diluted sterile brain heart infusion broth (BHIB) supplemented with a tissue culture grade antibiotic and antimycotic agent at concentrations sufficient for preventing the contamination by bacterial and fungi. Aseptic samples were taken to enumerate live *Uronema* on a daily basis to provide growth kinetics information.

Example 3

The ciliate was inoculated into different concentrations of diluted sterile tissue culture medium L-15) supplemented with a tissue culture grade antibiotic and antimycotic agent at concentrations sufficient for preventing the contamination by bacteria and fungi. Aseptic samples were taken to enumerate live *Uronema* on a daily basis to provide growth kinetics information.

Example 4

The ciliate was inoculated into sterile seawater supplemented with a tissue culture grade antibiotic and antimycotic agent at concentrations sufficient for preventing the contamination by bacteria and fungi. Zobaidy lateral muscle was added at different levels for supporting the growth of *Uronema* sp. Aseptic samples were taken to enumerate live *Uronema* on a daily basis to provide growth kinetics information.

Example 5

The ciliate was inoculated into different concentrations of diluted sterile brain heart infusion broth (BHIB). Additionally, a 24-h culture of *V. Alginolyticus* and/or *V. harveyi* was inoculated at the rate of $10^9$ CFU/mL (colony forming units/milliliter). Aseptic samples were taken to enumerate live *Uronema* on a daily basis to provide growth kinetics information and to enumerate encapsulated *V. alginolyticus* and/or *V. harveyi*.

Example 6

Custom-produced anti-*Uronema* antibodies were used to detect the immunogenicity of the formalin-inactivated *Uronema* sp. Commercial second antibody (Goat anti rabbit-HRP conjugate) was used to visualize the antigenicity of the formalin-inactivated *Uronema* sp. that is used for producing the oral vaccine. Anti-*Uronema* showed immune reactivity with the cilaiture.

Example 7

Sobaity juveniles (15±3.5 g), 5000/tank (1 ton capacity, in duplicates) were stocked, provided with aerated seawater in a flow-through system and orally vaccinated.

The fish were fed commercial diet (pellet feed) coated with formalin-inactivated *Uronema* at 106 cells/g of feed. The vaccine suspension was made in fish oil (a feed supplement) at a rate of 2.5% of the feed and the *Uronema* sp. cell density was adjusted accordingly to yield the required dose of 106 cells/g of feed.

The fish were fed 4-5 times a day for 10 days with vaccine incorporated feed and control feed according to the treatments. A 10-day vaccine diet and a 20-day control diet feeding protocol were followed to deliver a total of 4 vaccine feedings. Sampling for assessing growth, evaluating survival for assaying the immunological parameters from serum and mucus at 20, 40, 60, 80 and 110 days was carried out.

Example 8

The serum and mucus titers for agglutination/immobilization of formalin-inactivated *Uronema* sp. and *V. harveyii* were obtained using a "U" bottom microplate agglutination assay. The titers were expressed in $\log_2$ scale representing doubling dilutions of the serum or mucus.

Example 9

Information Re Zobaidy Vaccination Trial

The fish were fed with $10^6$ cells/g (feed), ad libitum, formalin inactivated *Uronema* spp. for 10 days as priming and booster doses.

*Uronema* inactivation percent as an index of anti *Uronema* factors in the mucus or orally vaccinated zobaidy.

Blue bars indicate inactivation of *Uronema* using the mucus of orally vaccinated zobaidy with priming dose (PR) for 10 days.

Relative inactivation is enhanced due to booster vaccination (BS) of a 10 day vaccine feeding after one month of priming vaccination.

Relative inactivation is expressed in enhanced percentage compared to the mucus of unvaccinated zobaidy fish.

While the invention has been disclosed in connection with its preferred embodiments it should be recognized that changes and modifications may be made therein without departing from the scope of the claims.

What is claimed is:

1. A method for vaccinating marine fish selected from the group consisting of Zobaidy (*Pampus argenteus Euphrasen*), Sobaity (*Sporidentax hastia*), hamoor against *Scuticociliatosis* and *Vibriosis*, said method consisting of feeding the fish four times a day for ten days of a food containing a vaccine comprising a formalin-killed whole cell of *Vibrio*-encapsulated *Uronema* spp.

2. A method for vaccinating marine fish selected from the group consisting of Zobaidy (*Pampus argenteus Euphrasen*), Sobaity (*Sporidentax hastia*), hamoor against *Scuticociliatosis* and *Vibriosis*, said method consisting of feeding the fish four times a day for ten days of a food containing the vaccine of claim 1 in which said *Vibrio* is selected from the group consisting of *Vibrio alginolyticus*, *Vibrio harveyi* and mixtures thereof.

3. A method for vaccinating marine fish selected from the group consisting of Zobaidy (*Pampus argenteus Euphrasen*), Sobaity (*Sporidentax hastia*), hamoor against *Scuticociliatosis* and *Vibriosis*, said method consisting of feeding the fish four times a day for ten days of a food containing the vaccine of claim 2 in which said *Vibrio* is *Vibrio alginolyticus*.

4. A method for vaccinating marine fish selected from the group consisting of Zobaidy (*Pampus argenteus Euphrasen*), Sobaity (*Sporidentax hastia*), hamoor against *Scuticociliatosis* and *Vibriosis*, said method consisting of feeding the fish four times a day for ten days of a food containing the vaccine of claim 2 in which said *Vibrio* is *Vibrio harveyi*.

* * * * *